(12) United States Patent
Andreas et al.

(10) Patent No.: US 7,300,456 B2
(45) Date of Patent: Nov. 27, 2007

(54) CUSTOM-LENGTH SELF-EXPANDING STENT DELIVERY SYSTEMS WITH STENT BUMPERS

(75) Inventors: Bernard Andreas, Redwood City, CA (US); Jeffry J. Grainger, Portola Valley, CA (US)

(73) Assignee: Xtent, Inc., Menlo Park, CA (US)

( * ) Notice: Subject to any disclaimer, the term of this patent is extended or adjusted under 35 U.S.C. 154(b) by 283 days.

(21) Appl. No.: 10/944,282

(22) Filed: Sep. 17, 2004

(65) Prior Publication Data

US 2005/0288763 A1 Dec. 29, 2005

Related U.S. Application Data

(63) Continuation-in-part of application No. 10/879,949, filed on Jun. 28, 2004.

(51) Int. Cl.
*A61F 2/06* (2006.01)
*A61M 29/02* (2006.01)

(52) U.S. Cl. ............... 623/1.12; 623/1.16; 604/101.01

(58) Field of Classification Search ............... 623/1.11, 623/1, 1.12, 1.2, 1.21, 1.23, 1.16, 1.13, 1.15; 606/108, 191, 192, 134, 195, 198; 604/93.01, 604/96.01, 101.01, 101.05
See application file for complete search history.

(56) References Cited

U.S. PATENT DOCUMENTS

| | | | |
|---|---|---|---|
| 4,468,224 A | 8/1984 | Enzmann et al. |
| 4,512,338 A | 4/1985 | Balko et al. |
| 4,564,014 A | 1/1986 | Fogarty et al. |
| 4,580,568 A | 4/1986 | Gianturco |
| 4,681,110 A | 7/1987 | Wiktor |
| 4,733,665 A | 3/1988 | Palmaz |
| 4,739,762 A | 4/1988 | Palmaz |
| 4,762,129 A | 8/1988 | Bonzel |

(Continued)

FOREIGN PATENT DOCUMENTS

EP 203945 B2 12/1986

(Continued)

OTHER PUBLICATIONS

Cooley et al., "Applications of Ink-Jet Printing Technology to BioMEMs and Microfluidic Systems," Proceedings, SPIE Conference on Microfluidics and BioMEMs, (Oct. 2001).

(Continued)

*Primary Examiner*—Glenn K. Dawson
*Assistant Examiner*—Kathleen Sonnett
(74) *Attorney, Agent, or Firm*—Townsend and Townsend and Crew LLP; J. Grainger, Esq.

(57) ABSTRACT

Custom-length self-expanding stent delivery systems and methods enable precise control of prosthesis position during deployment. The stent delivery systems carry multiple stent segments and include a stent bumper for helping control the axial position of the stent segments during deployment. This enables the deployment of multiple prostheses at a target site with precision and predictability, preventing stent segment recoil and ejection from the delivery device and thus eliminating excessive spacing or overlap between prostheses. In particular embodiments, the prostheses of the invention are deployed in stenotic lesions in coronary or peripheral arteries or in other vascular locations.

12 Claims, 7 Drawing Sheets

U.S. PATENT DOCUMENTS

| | | |
|---|---|---|
| 4,775,337 A | 10/1988 | Van Wagener et al. |
| 4,776,337 A | 10/1988 | Palmaz |
| 4,886,062 A | 12/1989 | Wiktor |
| 4,988,356 A | 1/1991 | Crittenden et al. |
| 4,994,066 A | 2/1991 | Voss |
| 4,994,069 A | 2/1991 | Ritchart et al. |
| 5,013,318 A | 5/1991 | Spranza, III |
| 5,040,548 A | 8/1991 | Yock |
| 5,092,877 A | 3/1992 | Pinchuk |
| 5,102,417 A | 4/1992 | Palmaz |
| 5,104,404 A | 4/1992 | Wolff |
| 5,135,535 A | 8/1992 | Kramer |
| 5,195,984 A | 3/1993 | Schatz |
| 5,217,495 A | 6/1993 | Kaplan et al. |
| 5,226,913 A | 7/1993 | Pinchuk |
| 5,246,421 A | 9/1993 | Saab |
| 5,273,536 A | 12/1993 | Savas |
| 5,282,824 A | 2/1994 | Gianturco |
| 5,300,085 A | 4/1994 | Yock |
| 5,312,415 A | 5/1994 | Palermo |
| 5,334,187 A | 8/1994 | Fischell et al. |
| 5,421,955 A | 6/1995 | Lau et al. |
| 5,458,615 A | 10/1995 | Klemm et al. |
| 5,478,349 A | 12/1995 | Nicholas |
| 5,490,837 A | 2/1996 | Blaeser et al. |
| 5,496,346 A | 3/1996 | Horzewski et al. |
| 5,501,227 A | 3/1996 | Yock |
| 5,507,768 A | 4/1996 | Lau et al. |
| 5,507,771 A | 4/1996 | Gianturco |
| 5,514,093 A | 5/1996 | Ellis et al. |
| 5,514,154 A | 5/1996 | Lau et al. |
| 5,527,354 A | 6/1996 | Fontaine et al. |
| 5,549,551 A | 8/1996 | Peacock, III et al. |
| 5,549,563 A | 8/1996 | Kronner |
| 5,549,635 A | 8/1996 | Solar |
| 5,554,181 A | 9/1996 | Das |
| 5,562,725 A | 10/1996 | Schmitt et al. |
| 5,571,086 A | 11/1996 | Kaplan et al. |
| 5,593,412 A | 1/1997 | Martinez et al. |
| 5,607,444 A | 3/1997 | Lam |
| 5,607,463 A | 3/1997 | Schwartz et al. |
| 5,628,775 A | 5/1997 | Jackson et al. |
| 5,634,928 A | 6/1997 | Fischell et al. |
| 5,662,675 A | 9/1997 | Polanskyj Stockert et al. |
| 5,676,654 A | 10/1997 | Ellis et al. |
| 5,683,451 A | 11/1997 | Lenker et al. |
| 5,697,948 A | 12/1997 | Marin et al. |
| 5,702,418 A | 12/1997 | Ravenscroft |
| 5,709,701 A | 1/1998 | Parodi |
| 5,722,669 A | 3/1998 | Shimizu et al. |
| 5,723,003 A | 3/1998 | Winston et al. |
| 5,735,869 A | 4/1998 | Fernandez-Aceytuno |
| 5,749,848 A | 5/1998 | Jang et al. |
| 5,749,890 A * | 5/1998 | Shaknovich ............ 606/198 |
| 5,749,921 A | 5/1998 | Lenker et al. |
| 5,755,772 A | 5/1998 | Evans et al. |
| 5,755,776 A | 5/1998 | Al-Saadon |
| 5,755,781 A | 5/1998 | Jayaraman |
| 5,769,882 A | 6/1998 | Fogarty et al. |
| 5,772,669 A | 6/1998 | Vrba |
| 5,776,141 A | 7/1998 | Klein et al. |
| 5,800,519 A | 9/1998 | Sandock |
| 5,807,398 A | 9/1998 | Shaknovich |
| 5,824,040 A | 10/1998 | Cox et al. |
| 5,824,041 A | 10/1998 | Lenker et al. |
| 5,833,694 A | 11/1998 | Poncet |
| 5,836,964 A | 11/1998 | Richter et al. |
| 5,843,092 A | 12/1998 | Heller et al. |
| 5,858,556 A | 1/1999 | Eckert et al. |
| 5,870,381 A | 2/1999 | Kawasaki et al. |
| 5,879,370 A | 3/1999 | Fischell et al. |
| 5,891,190 A | 4/1999 | Boneau |
| 5,895,398 A | 4/1999 | Wensel et al. |
| 5,899,935 A | 5/1999 | Ding |
| 5,902,332 A | 5/1999 | Schatz |
| 5,919,175 A | 7/1999 | Sirhan |
| 5,922,020 A | 7/1999 | Klein et al. |
| 5,961,536 A | 10/1999 | Mickley et al. |
| 5,968,069 A * | 10/1999 | Dusbabek et al. .......... 606/194 |
| 5,976,107 A | 11/1999 | Mertens et al. |
| 5,976,155 A | 11/1999 | Foreman et al. |
| 5,980,484 A | 11/1999 | Ressemann et al. |
| 5,980,486 A | 11/1999 | Enger |
| 5,980,514 A | 11/1999 | Kupiecki et al. |
| 5,980,552 A | 11/1999 | Pinchasik et al. |
| 5,984,957 A | 11/1999 | Laptewicz, Jr. et al. |
| 6,007,517 A | 12/1999 | Anderson |
| 6,022,359 A | 2/2000 | Frantzen |
| 6,033,434 A | 3/2000 | Borghi |
| 6,039,721 A | 3/2000 | Johnson et al. |
| 6,042,589 A | 3/2000 | Marianne |
| 6,056,722 A | 5/2000 | Jayaraman |
| 6,066,155 A | 5/2000 | Amann et al. |
| 6,068,655 A | 5/2000 | Seguin et al. |
| 6,090,063 A | 7/2000 | Makower et al. |
| 6,090,136 A | 7/2000 | McDonald et al. |
| 6,102,942 A | 8/2000 | Ahari |
| 6,106,530 A | 8/2000 | Harada |
| RE36,857 E | 9/2000 | Euteneuer et al. |
| 6,120,522 A | 9/2000 | Vrba et al. |
| 6,123,712 A | 9/2000 | Di Caprio et al. |
| 6,123,723 A | 9/2000 | Konya et al. |
| 6,126,685 A | 10/2000 | Lenker et al. |
| 6,129,756 A | 10/2000 | Kugler |
| 6,143,016 A * | 11/2000 | Bleam et al. ............... 606/198 |
| 6,165,167 A | 12/2000 | Delaloye |
| 6,179,878 B1 | 1/2001 | Duering |
| 6,187,034 B1 | 2/2001 | Frantzen |
| 6,190,402 B1 | 2/2001 | Horton et al. |
| 6,196,995 B1 | 3/2001 | Fagan |
| 6,200,337 B1 | 3/2001 | Moriuchi et al. |
| 6,241,691 B1 | 6/2001 | Ferrera et al. |
| 6,251,132 B1 * | 6/2001 | Ravenscroft et al. ...... 623/1.11 |
| 6,251,134 B1 | 6/2001 | Alt et al. |
| 6,254,612 B1 | 7/2001 | Hieshima |
| 6,254,628 B1 | 7/2001 | Wallace et al. |
| 6,258,117 B1 | 7/2001 | Camrud et al. |
| 6,267,783 B1 | 7/2001 | Letendre et al. |
| 6,273,895 B1 | 8/2001 | Pinchuk et al. |
| 6,273,913 B1 | 8/2001 | Wright et al. |
| 6,312,458 B1 | 11/2001 | Golds |
| 6,315,794 B1 | 11/2001 | Richter |
| 6,319,277 B1 | 11/2001 | Rudnick et al. |
| 6,325,823 B1 | 12/2001 | Horzewski et al. |
| 6,357,104 B1 | 3/2002 | Myers |
| 6,375,676 B1 | 4/2002 | Cox |
| 6,383,171 B1 | 5/2002 | Gifford et al. |
| 6,419,693 B1 | 7/2002 | Fariabi |
| 6,451,025 B1 | 9/2002 | Jervis |
| 6,451,050 B1 | 9/2002 | Rudakov et al. |
| 6,468,298 B1 | 10/2002 | Pelton |
| 6,468,299 B2 | 10/2002 | Stack et al. |
| 6,485,510 B1 | 11/2002 | Camrud et al. |
| 6,488,694 B1 | 12/2002 | Lau et al. |
| 6,488,702 B1 | 12/2002 | Besselink |
| 6,511,468 B1 | 1/2003 | Cragg et al. |
| 6,520,987 B1 | 2/2003 | Plante |
| 6,527,789 B1 | 3/2003 | Lau et al. |
| 6,527,799 B2 | 3/2003 | Shanley |
| 6,555,157 B1 | 4/2003 | Hossainy |
| 6,575,993 B1 | 6/2003 | Yock |
| 6,582,394 B1 | 6/2003 | Reiss et al. |
| 6,529,549 B1 | 7/2003 | Gerdts et al. |
| 6,599,296 B1 | 7/2003 | Gillick et al. |

| | | | |
|---|---|---|---|
| 6,602,282 B1 | 8/2003 | Yan | |
| 6,605,062 B1 | 8/2003 | Hurley et al. | |
| 6,645,547 B1 | 11/2003 | Shekalim et al. | |
| 6,656,212 B2 | 12/2003 | Ravenscroft et al. | |
| 6,666,883 B1 | 12/2003 | Seguin et al. | |
| 6,679,909 B2 | 1/2004 | McIntosh et al. | |
| 6,692,465 B2 | 2/2004 | Kramer | |
| 6,702,843 B1 * | 3/2004 | Brown et al. | 623/1.11 |
| 6,712,827 B2 | 3/2004 | Ellis et al. | |
| 6,712,845 B2 | 3/2004 | Hossainy | |
| 6,723,071 B2 | 4/2004 | Gerdts et al. | |
| 6,743,251 B1 | 6/2004 | Eder | |
| 6,800,065 B2 | 10/2004 | Duane et al. | |
| 6,849,084 B2 | 2/2005 | Rabkin et al. | |
| 2001/0020154 A1 | 9/2001 | Bigus et al. | |
| 2001/0020181 A1 | 9/2001 | Layne | |
| 2001/0044595 A1 | 11/2001 | Reydel et al. | |
| 2002/0037358 A1 | 3/2002 | Barry et al. | |
| 2002/0107560 A1 | 8/2002 | Richter | |
| 2002/0138132 A1 | 9/2002 | Brown | |
| 2002/0151955 A1 * | 10/2002 | Tran et al. | 623/1.12 |
| 2002/0156496 A1 | 10/2002 | Chermoni | |
| 2002/0177890 A1 | 11/2002 | Lenker | |
| 2002/0188343 A1 | 12/2002 | Mathis | |
| 2002/0188347 A1 | 12/2002 | Mathis | |
| 2002/0193873 A1 | 12/2002 | Brucker et al. | |
| 2003/0045923 A1 | 3/2003 | Bashiri et al. | |
| 2003/0093143 A1 | 5/2003 | Zhao et al. | |
| 2003/0097169 A1 | 5/2003 | Brucker et al. | |
| 2003/0114912 A1 | 6/2003 | Sequin et al. | |
| 2003/0114919 A1 * | 6/2003 | McQuiston et al. | 623/1.15 |
| 2003/0114922 A1 | 6/2003 | Iwasaka et al. | |
| 2003/0125791 A1 | 7/2003 | Sequin et al. | |
| 2003/0135266 A1 | 7/2003 | Chew et al. | |
| 2003/0139796 A1 | 7/2003 | Sequin et al. | |
| 2003/0139797 A1 | 7/2003 | Johnson et al. | |
| 2003/0176909 A1 | 9/2003 | Kusleika | |
| 2003/0199821 A1 | 10/2003 | Gerdts et al. | |
| 2003/0225446 A1 | 12/2003 | Hartley | |
| 2004/0087965 A1 | 5/2004 | Levine et al. | |
| 2004/0093061 A1 | 5/2004 | Acosta et al. | |
| 2004/0093067 A1 | 5/2004 | Israel | |
| 2004/0098081 A1 | 5/2004 | Landreville et al. | |
| 2004/0186551 A1 | 9/2004 | Kao et al. | |
| 2004/0215165 A1 | 10/2004 | Coyle et al. | |
| 2004/0215312 A1 | 10/2004 | Andreas | |
| 2004/0249435 A1 * | 12/2004 | Andreas et al. | 623/1.12 |
| 2005/0010276 A1 | 1/2005 | Acosta et al. | |
| 2005/0038505 A1 | 2/2005 | Shuize et al. | |
| 2005/0133164 A1 | 6/2005 | Andreas et al. | |
| 2005/0149159 A1 | 7/2005 | Andreas et al. | |
| 2005/0288763 A1 | 12/2005 | Andreas et al. | |
| 2006/0229700 A1 | 10/2006 | Acosta et al. | |
| 2006/0282147 A1 | 12/2006 | Andreas et al. | |
| 2006/0282150 A1 | 12/2006 | Olson et al. | |

FOREIGN PATENT DOCUMENTS

| | | |
|---|---|---|
| EP | 274129 B1 | 7/1988 |
| EP | 282143 | 9/1988 |
| EP | 0 505 686 | 9/1992 |
| EP | 0 533 960 | 3/1993 |
| EP | 0 596 145 | 5/1997 |
| EP | 947180 | 10/1999 |
| EP | 1266638 B1 | 10/2005 |
| WO | WO 96/33677 | 10/1996 |
| WO | WO 97/46174 | 12/1997 |
| WO | WO 97/48351 | 12/1997 |
| WO | WO 99/01087 | 1/1999 |
| WO | WO 00/15151 | 3/2000 |
| WO | WO 00/32136 | 6/2000 |
| WO | WO 00/41649 | 7/2000 |
| WO | WO0072780 A1 * | 7/2000 |
| WO | WO 00/50116 | 8/2000 |
| WO | WO 00/62708 | 10/2000 |
| WO | WO 00/72780 | 12/2000 |
| WO | WO 01/70297 | 9/2001 |
| WO | WO 01/91918 | 12/2001 |
| WO | WO 03/022178 | 3/2003 |
| WO | WO 03/047651 | 6/2003 |
| WO | WO 03/051425 | 6/2003 |
| WO | WO 2004/017865 | 3/2004 |
| WO | WO 2004/043299 | 5/2004 |
| WO | WO 2004/043301 | 5/2004 |
| WO | WO 2004/043510 | 5/2004 |
| WO | WO 2004/052237 | 6/2004 |

OTHER PUBLICATIONS

Colombo, "The Invatec Bifurcation Stent Solution" Bifurcation Stents: Novel Solutions, TCT 2003, Washington: Sep. 15-19, 2003, 24 pages total.

Lefevre et al. "Approach to Coronary Bifurcation Stenting in 2003," Euro PCR, (May 2003) 28 pages total.

"Stent". Definitions from Dictionary.com. Unabridged (v1.01). Retrieved Sep. 22, 2006, from Dictionary.com website: <http://dictionary.reference.com/search?q=stent>.

Stimpson et al, Parallel Production of Oligonucleotide Arrays Using Membranes and Reagent Jet Printing, BioTechniques 25:886-890 (Nov. 1998).

Colombo, "The Invatec Bifurcation Stent Solution" Birfucation Stents: Novel Solutions, TCT 2003, Washington: Sep. 15-19, 2003, 24 pages total.

* cited by examiner

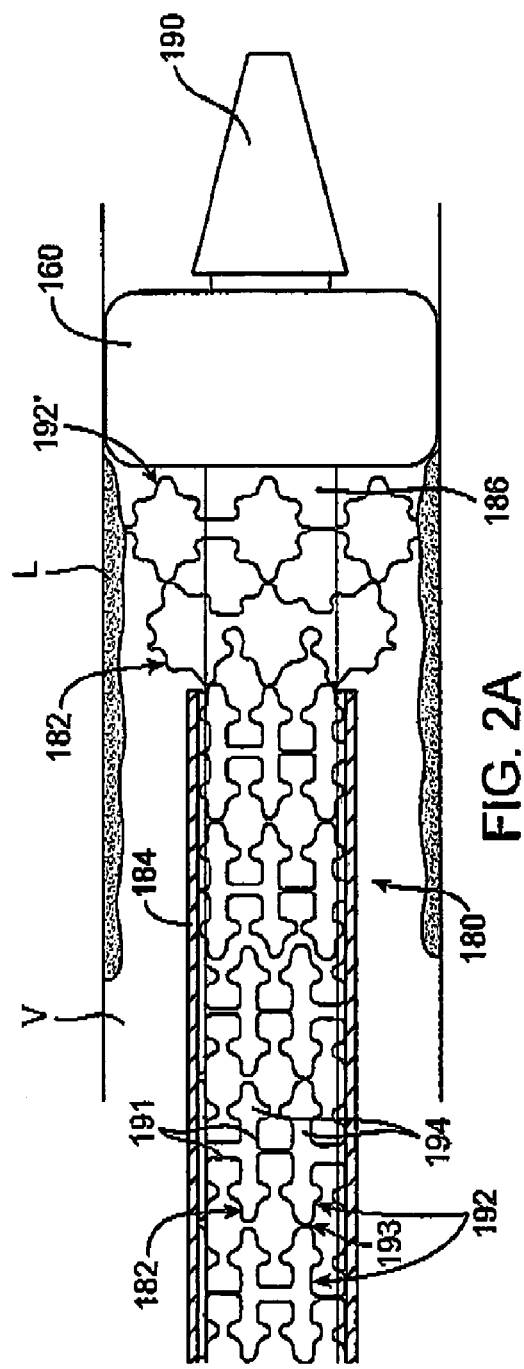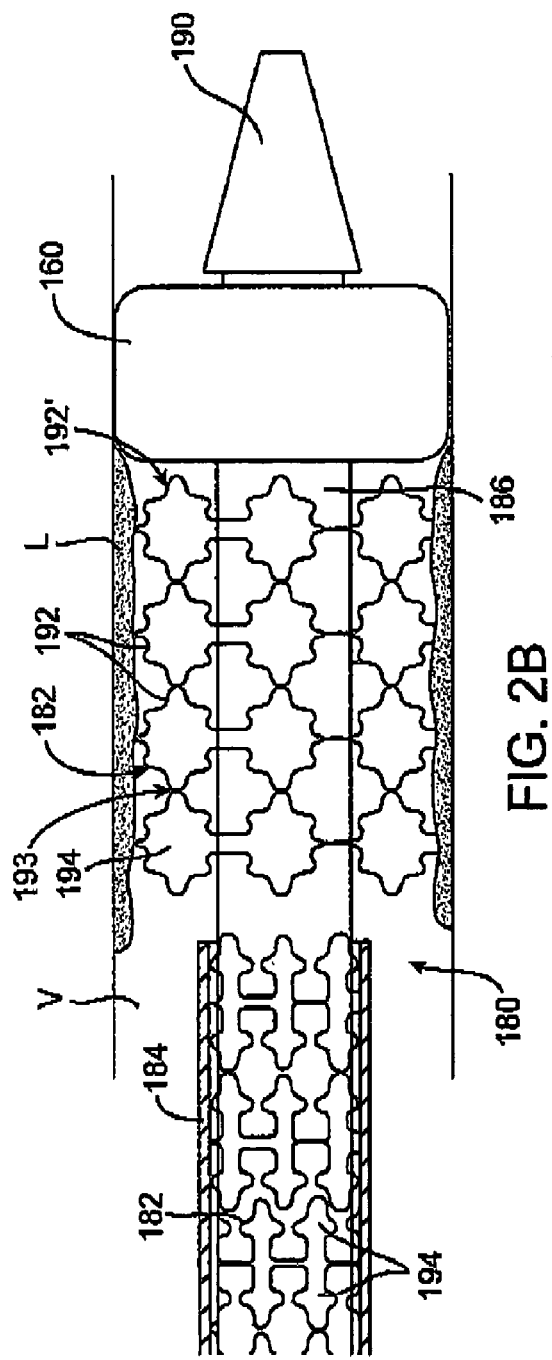
FIG. 2A
FIG. 2B

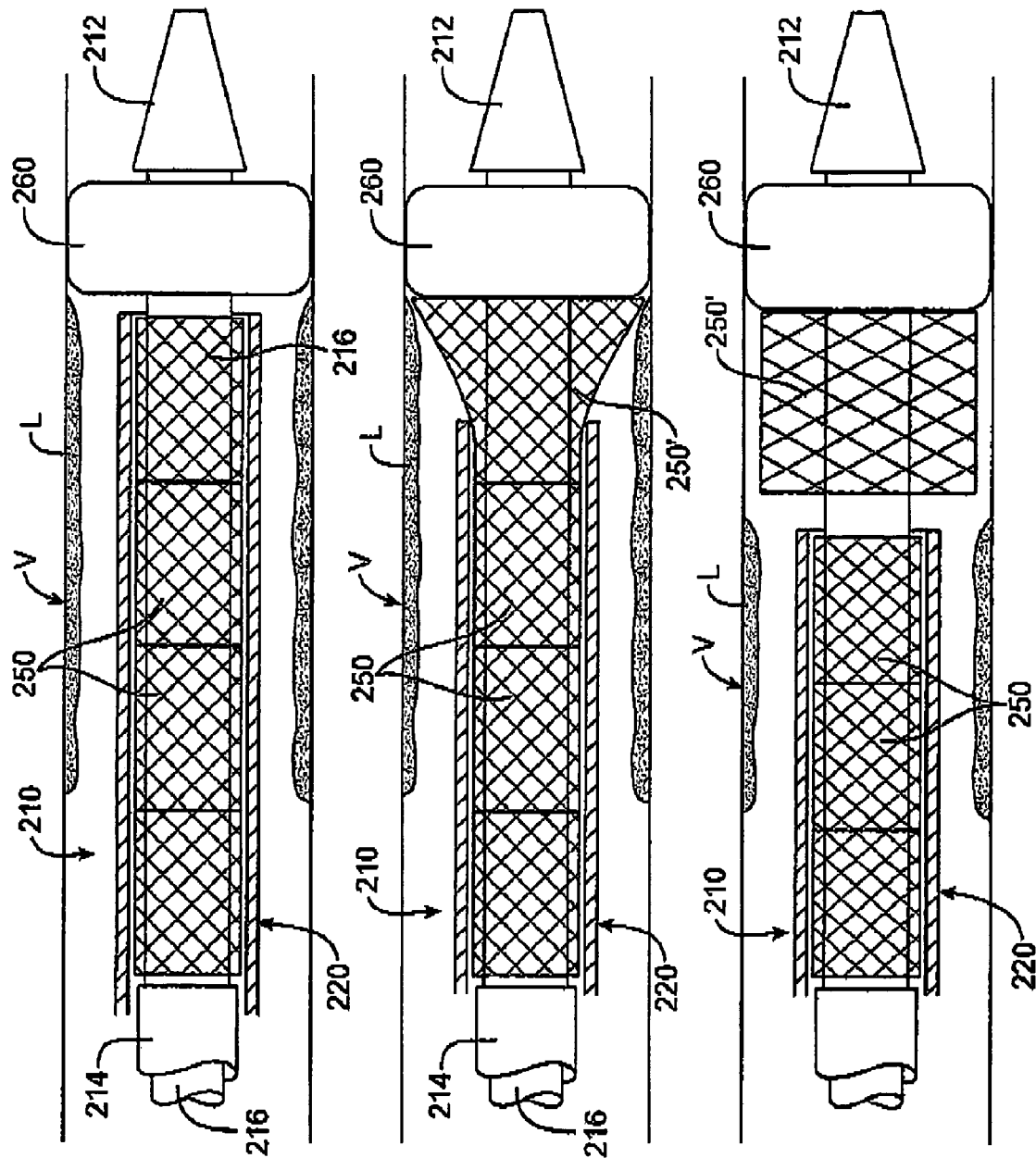

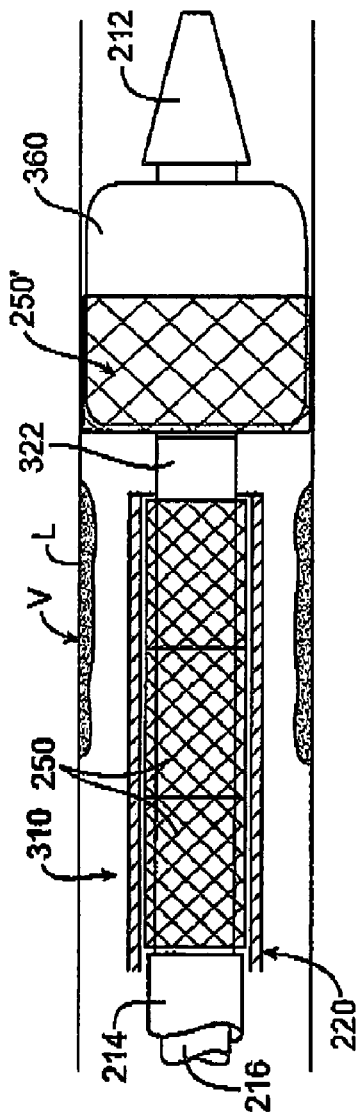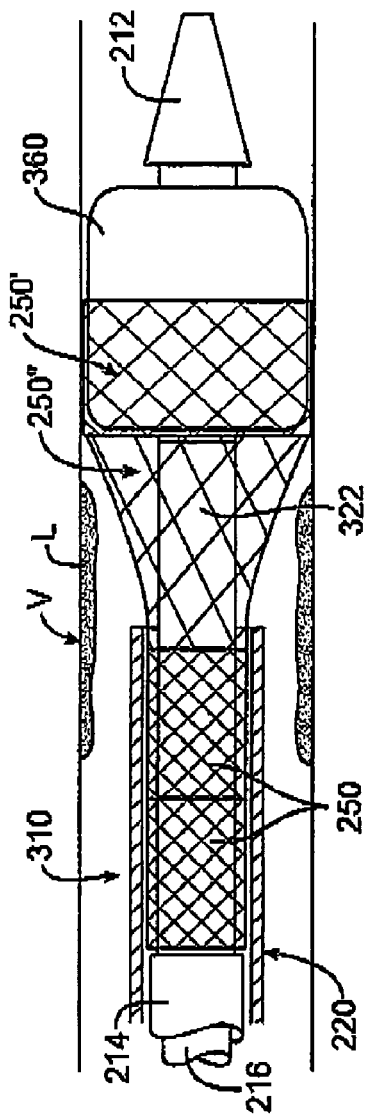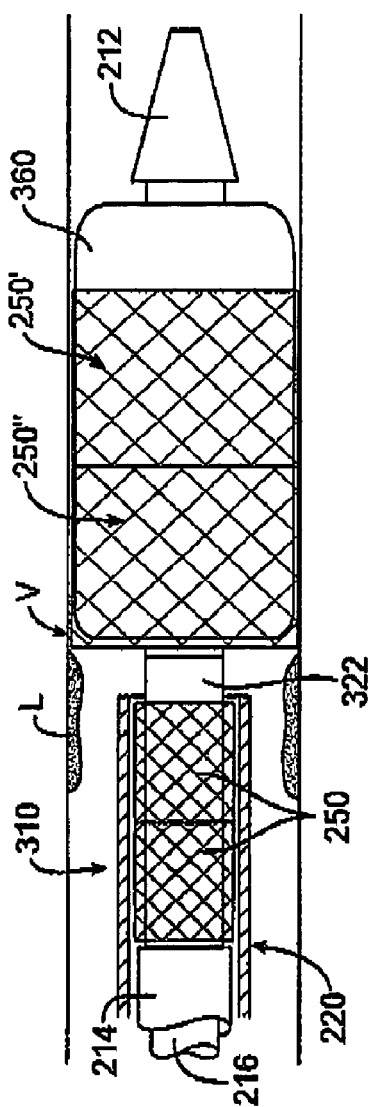

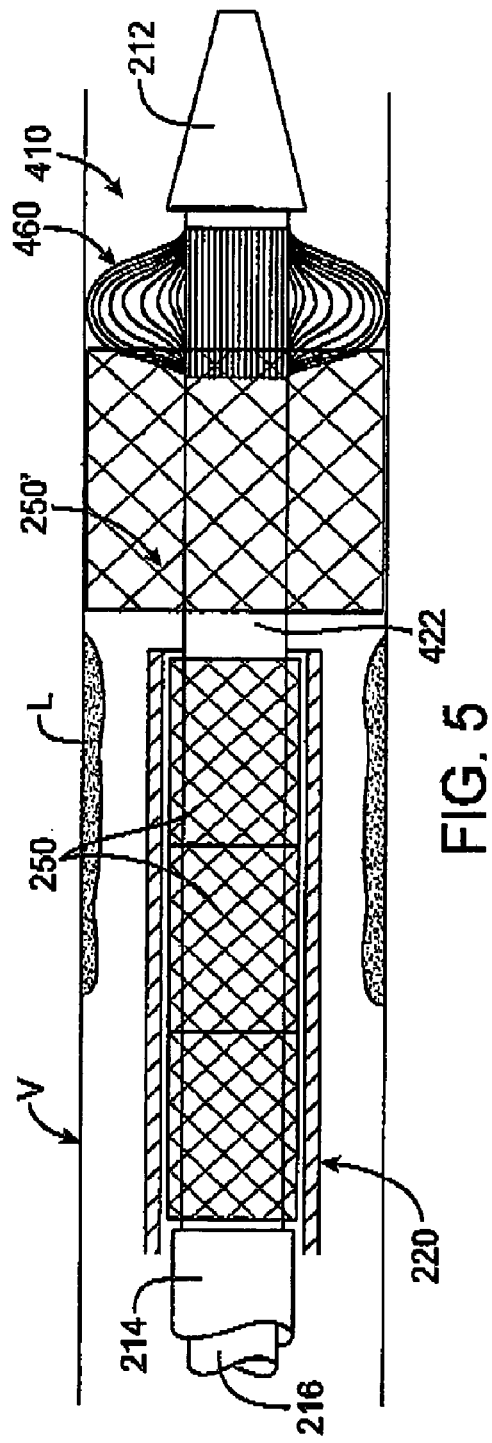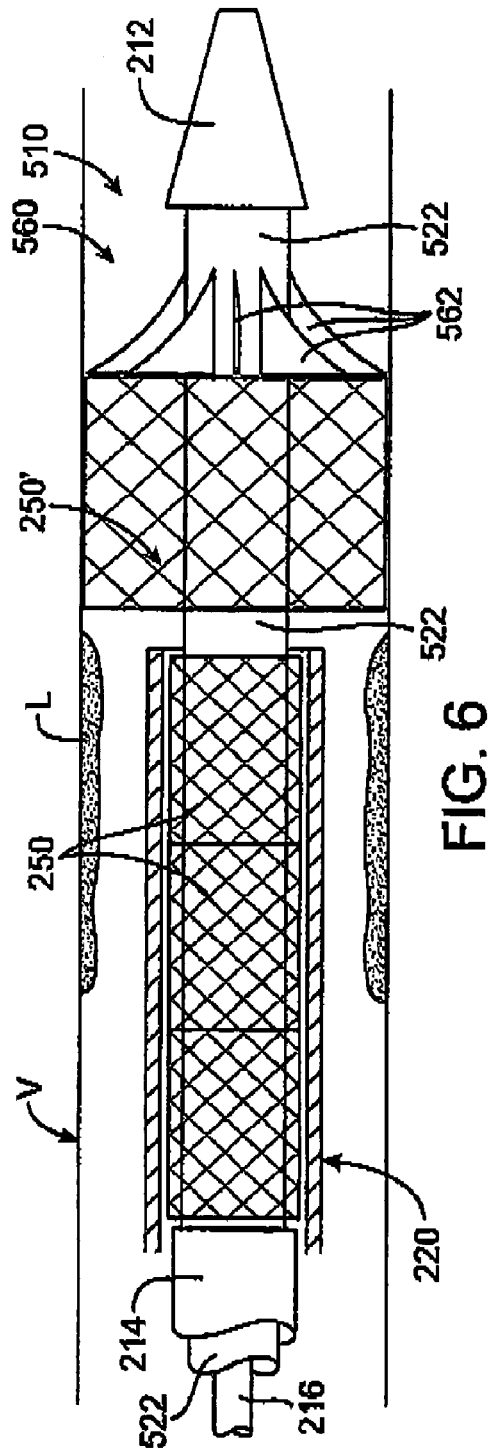

ns system that overcome the foregoing problems. In particular,
CUSTOM-LENGTH SELF-EXPANDING STENT DELIVERY SYSTEMS WITH STENT BUMPERS

CROSS REFERENCE TO RELATED APPLICATIONS

This application is a continuation-in-part of U.S. patent application Ser. No. 10/879,949, filed Jun. 28, 2004, which is hereby incorporated fully by reference.

BACKGROUND OF THE INVENTION

Stents are tubular prostheses designed for implantation in a vessel to maintain patency of the vessel lumen. Stents are used in various vessels throughout the body, including the coronary arteries, femoral arteries, iliac arteries, renal artery, carotid artery, vascular grafts, biliary ducts, trachea, and urethra. Stents are typically implanted by means of long, flexible delivery catheters that carry the stents in a compact, collapsed shape to the treatment site and then deploy the stents into the vessel. In some applications, balloon expandable stents are used. These stents are made of a malleable metal such as stainless steel or cobalt chromium and are expanded by means of a balloon on the tip of the delivery catheter to plastically deform the stent into contact with the vessel wall. In other applications, self-expanding stents are used. These are made of a resilient material that can be collapsed into a compact shape for delivery via catheter and that will self-expand into contact with the vessel when deployed from the catheter. Materials commonly used for self-expanding stents include stainless steel and elastic or superelastic alloys such as nickel titanium (Nitinol™).

While self-expanding stents have demonstrated promise in various applications, such stents face a number of challenges. One such challenge is that in some cases the disease in a vessel may be so extensive that a stent of very long length, e.g. 30-200 mm, is called for. Currently available stents are typically less than 30 mm in length, and suffer from excessive stiffness if made longer. Such stiffness is particularly problematic in peripheral vessels such as the femoral arteries, where limb movement requires a high degree of flexibility in any stent implanted in such vessels.

To overcome the stiffness problem, the idea of deploying multiple shorter stents end-to-end has been proposed. However, this approach has suffered from several drawbacks. First, currently available delivery catheters are capable of delivering only a single stent per catheter. In order to place multiple stents, multiple catheters must be inserted, removed and exchanged, heightening risks, lengthening procedure time, raising costs, and causing excessive material waste. In addition, the deployment of multiple stents end-to-end suffers from the inability to accurately control stent placement and the spacing between stents. This results in overlap of adjacent stents and/or excessive space between stents, which is thought to lead to complications such as restenosis, the renarrowing of a vessel following stent placement. With self-expanding stents the problem is particularly acute, because as the stent is released from the catheter, its resiliency tends to cause it to eject or "watermelon seed" distally from the catheter tip by an unpredictable distance. During such deployment, the stent may displace not only axially but rotationally relative to the delivery catheter resulting in inaccurate, uncontrollable, and unpredictable stent placement.

Interleaving stents or stent segments such as those disclosed in co-pending U.S. patent application Ser. No. 10/738,666, filed Dec. 16, 2003, which is incorporated herein by reference, present even greater challenges to conventional delivery systems. Interleaving stents have axially extending elements on each end of the stent that interleave with similar structures on an adjacent stent. Such interleaving minimizes the gap between adjacent stents and increases vessel wall coverage to ensure adequate scaffolding and minimize protrusion of plaque from the vessel wall. However, such interleaving requires that the relative rotational as well as axial positions of the adjacent stents be maintained during deployment to avoid metal overlap and excessive gaps between stents. Conventional delivery systems suffer from the inability to control both the axial and rotational positions of self-expanding stents as they are deployed. These issues are addressed, in part, in co-pending U.S. patent application Ser. No. 10/879,949, which was previously incorporated by reference. "Watermelon seeding" of self-expanding stents, where the resiliency of the stents causes them to eject distally from the catheter tip by an unpredictable distance, continues to be a challenge.

What are needed, therefore, are stents and stent delivery the stents and stent delivery systems should facilitate stenting of long vascular regions of various lengths without requiring the use of multiple catheters. Such stents and delivery systems should also provide sufficient flexibility for use in peripheral vessels and other regions where long and highly flexible stents might be required. In addition, the stents and stent delivery systems should enable the delivery of multiple stents of various lengths to one or more treatment sites using a single catheter without requiring catheter exchanges. Further, the stents and stent delivery systems should facilitate accurate and repeatable control of stent placement and inter-stent spacing to enable deployment of multiple self-expanding stents end-to-end in a vessel at generally constant spacing and without overlap. In particular, the stents and delivery systems should enable the deployment of interleaving stents or stent segments with precision and control over the axial spacing of each stent or segment.

BRIEF SUMMARY OF THE INVENTION

The present invention provides prostheses, prosthesis delivery systems, and methods of prosthesis deployment that enable the precise and controllable delivery of multiple prostheses using a single delivery catheter. The prostheses, delivery systems, and methods of the invention provide for the precise control of prosthesis placement so that inter-prosthesis spacing is maintained at a constant and optimum distance. In some embodiments, both axial and rotational displacement of the prostheses relative to the delivery catheter is controlled during deployment, enabling the delivery of multiple prostheses that interleave with one another without overlap. Moreover, with the use of drug-coated stents, it may be possible to place the stents apart by discrete distances, typically from one-half to one millimeter (mm), while still achieving vessel patency and hyperplasia inhibition. The prostheses, prosthesis delivery systems, and methods of the invention further enable the length of prostheses to be customized in situ to match the length of the site to be treated. The invention is particularly useful for delivery of self-expanding prostheses, but balloon expandable prostheses are also contemplated within the scope of the invention. The invention is well-suited to delivery of stents to the coronary arteries and to peripheral vessels such as the popliteal, femoral, tibial, iliac, renal, and carotid arteries. The invention is further useful for delivery of prostheses to other vessels including biliary, neurologic, urinary, reproductive, intestinal, pulmonary, and others, as well as for delivery of other types of prostheses to various anatomical regions, wherever precise control of prosthesis deployment is desirable.

In a first aspect of the invention, a catheter system for delivery of a stent to a body lumen includes a stent delivery catheter and a plurality of stent segments. The stent delivery catheter includes a sheath having a first lumen, a shaft extending through the first lumen and slidable relative to the sheath, and a stent bumper mounted to the shaft distally of the sheath and movable from a contracted shape to an expanded shape. The plurality of self-expanding stent segments is carried within the first lumen in a collapsed configuration, and the segments are adapted to resiliently expand from the collapsed configuration to an expanded configuration. The stent segments are deployable from the first lumen so as to expand into the expanded configuration, while the stent bumper is configured to engage a first stent segment during deployment thereof to maintain its position relative to an adjacent stent segment disposed proximal to the first stent segment.

In a number of embodiments, the stent bumper in the expanded shape has an outer diameter sized to contact an inner wall of the body lumen. The bumper may thus prevent distal migration of the stent segments and be stable in the vessel, without tilting, deflecting or slipping. In some embodiments, at least a portion of the stent bumper includes a lubricious surface for contacting one or more of the stent segments. For example, a proximal surface or portion of the stent bumper may have such a coating.

The bumper itself may have any of a number of suitable shapes, sizes and configurations, and may be made of any suitable material or combinations of materials. In some embodiments, for example, the stent bumper may comprise an expandable basket, a plurality of expandable blades, rods or petals, an expandable disk, a proximal portion of a nosecone at the distal end of the catheter shaft, or the like. In a preferred embodiment, the stent bumper comprises an inflatable balloon. In such embodiments, the catheter typically further includes an inflation lumen in the shaft (or elsewhere in the catheter), which is in fluid communication with the inflatable balloon. In some embodiments, the balloon is adapted to be deflated, positioned within the deployed first stent segment, and re-inflated to the expanded shape. Optionally, the balloon in the expanded shape may be adapted to further expand the deployed first stent segment. In an alternative embodiment, an elongate balloon is used, the balloon having an axial length at least as long as two stent segments. In one embodiment, for example, the axial length of the elongate balloon is between about 20 mm and about 250 mm. In such embodiments, the catheter may further include an inner sheath disposed over the balloon, with the inner sheath being retractable to expose a portion of the balloon to allow it to be inflated from the contracted shape to the expanded shape. In some embodiments, the balloon is adapted to be expanded within one or more deployed stent segments to further expand the segments.

Any suitable stents or stent segments may be used. Examples of self-expanding stents are described in U.S. patent application Ser. No. 10/879,949, which was previously incorporated by reference, but any other suitable self-expanding stents or stent segments may be substituted in various embodiment. In some embodiments, balloon expandable stents may be used. In various embodiments, the stent segments may be made of Nitinol, other superelastic alloys, stainless steel, cobalt chromium, other resilient metals, polymers or any other suitable material. Additionally, each stent segment may have any suitable length. In some embodiments, for example, each stent segment has a length of between about 3 mm and about 30 mm, and more preferably between about 4 mm and about 20 mm. Furthermore, any suitable number of stent segments may be loaded onto the catheter in various embodiments. For example, some embodiments may include between 2 and 50 segments. In some embodiments, the catheter may additionally include a pusher slidably disposed over the shaft, proximal to the stent segments, for advancing the stent segments relative to the sheath or holding the stent segments in place while the sheath is retracted.

In another aspect of the invention, a method of delivering a stent to a body lumen involves: positioning a stent delivery catheter in the body lumen, the delivery catheter carrying at least first and second stent segments; expanding a stent bumper on the delivery catheter; releasing the first stent segment from the delivery catheter into the body lumen proximal to the stent bumper, the first stent segment self-expanding into an expanded configuration in the body lumen, wherein the stent bumper engages the first stent segment during expansion thereof to maintain its position relative to the delivery catheter; and releasing the second stent segment from the delivery catheter into the body lumen adjacent to the first stent segment.

In a preferred embodiment, expanding the stent bumper involves inflating a balloon. Optionally, such a method may further include, before releasing the second stent segment: deflating the balloon; positioning the deflated balloon within the expanded first stent segment; and inflating the balloon, wherein the balloon engages the second stent segment during expansion thereof to maintain its position relative to the delivery catheter and the first segment. In some embodiments, inflating the balloon within the first segment further expands the first segment. The method may further involve: deflating the balloon; positioning the deflated balloon within the expanded second stent segment; and inflating the balloon, wherein the balloon engages a third stent segment during expansion thereof to maintain its position relative to the delivery catheter and the first and second segments. These steps of deflating, positioning and inflating may be repeated as many times as desired to deploy a desired number of stent segments.

In an alternative embodiment, before expanding the balloon, a portion of the balloon is exposed from the distal end of an inner sheath that is disposed over the balloon. Such a method may optionally further involve, before releasing the second stent segment: exposing an additional portion of the balloon from the distal end of the inner sheath, the additional portion disposed within the expanded first stent segment; and inflating the balloon, wherein the balloon engages the second stent segment during expansion thereof to maintain its position relative to the delivery catheter and the first segment. In some embodiments, inflating the additional portion of the balloon further expands the expanded first stent segment.

Rather than inflating a balloon, in alternative embodiments expanding the stent bumper involves deploying one or more other structures on the catheter device. In one embodiment, for example, a basket of resilient polymer or metal mesh is expanded. In some embodiments, expanding the stent bumper involves releasing one or more shape-memory members from constraint. For example, the shape-memory member(s) may include blades, rods, petals, rings or the like, made of metal, polymer or other resilient material.

The stents may be released from the delivery catheter via any suitable means. In one embodiment, for example, releasing each stent segment involves maintaining an axial position of the stent segments relative to the delivery catheter using a pusher member of the catheter and retracting an outer sheath disposed over the stent segments. Alternatively, releasing each stent segment may involve maintaining an axial position of an outer sheath disposed over the stent segments relative to the delivery catheter and advancing the stent segments out of a distal end of the sheath using a pusher member of the catheter.

Further aspects of the nature and advantages of the invention will be apparent from the following detailed description of various embodiments of the invention taken in conjunction with the drawings.

BRIEF DESCRIPTION OF THE DRAWINGS

FIGS. 2A and 2B are side cross-sectional views of a distal portion of a prosthesis delivery catheter with a stent bumper in a vessel according to one embodiment of the present invention, showing outer shaft retracted with prosthesis partially deployed, and prosthesis fully deployed, respectively.

FIGS. 3A-3F are side cross-sectional views of a distal portion of a prosthesis delivery catheter with a stent bumper in a vessel according to one embodiment of the present invention, demonstrating a method for deploying stents in a vessel.

FIGS. 4A-4C are side cross-sectional view of a distal portion of a prosthesis delivery catheter with a stent bumper in a vessel according to another embodiment of the present invention, demonstrating an alternative method for deploying stents in a vessel.

FIG. 5 is a side cross-sectional view of a distal portion of a prosthesis delivery catheter with a stent bumper in a vessel according to another embodiment of the present invention.

FIG. 6 is a side cross-sectional view of a distal portion of a prosthesis delivery catheter with a stent bumper in a vessel according to another embodiment of the present invention.

DETAILED DESCRIPTION OF THE INVENTION

Figure 1:
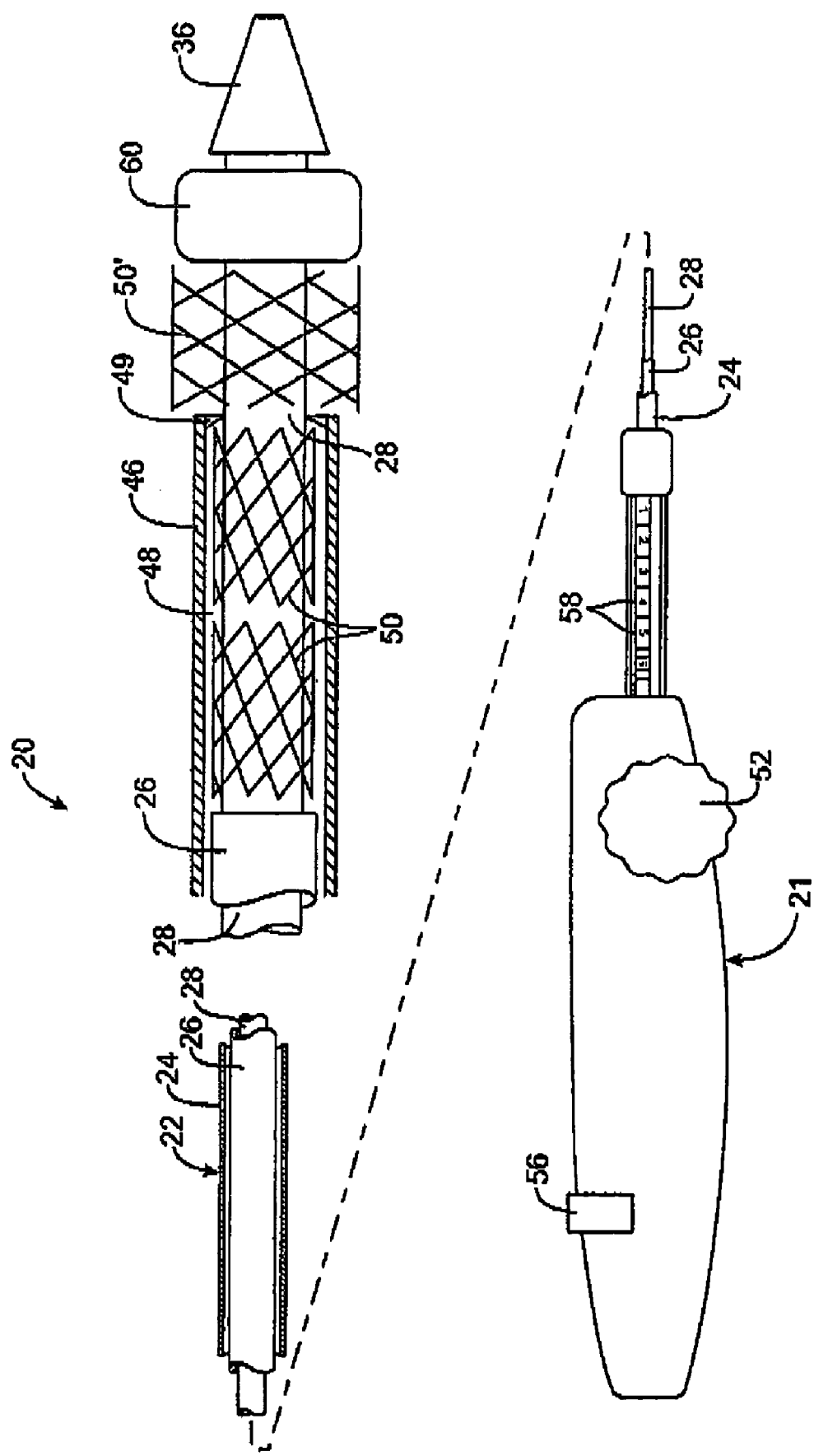
FIG. 1 is a side, partially cut-away view of a prosthesis delivery catheter according to one embodiment of the present invention.

Referring to FIG. 1, a first embodiment of a prosthesis delivery catheter 20 according to the invention is illustrated. Delivery catheter 20 may have any of various constructions, including those described in co-pending U.S. patent application Ser. Nos. 10/637,713, filed Aug. 8, 2003; 10/874,859, filed Jun. 22, 2004; and 10/884,616, filed Jul. 2, 2004, all of which are hereby incorporated by reference. Delivery catheter 20 has a handle assembly 21 and an elongated catheter body 22 that includes three concentric tubular shafts, all axially slidable relative to one another: an outer shaft 24, a pusher 26, and an inner shaft 28. A distal portion of delivery catheter 20 is shown schematically and in partial cutaway view for clarity. The distal portion, as well as other portions of delivery catheter 20 may include additional features not shown. For example, a typical embodiment includes a guidewire tube/lumen for allowing passage of a guidewire. Such features are described in further detail, for example, in the co-pending patent applications described immediately above.

Outer shaft 24 has a distal extremity 46 defining a first lumen 48. A plurality of stents 50 (or stent segments) are disposed in a collapsed configuration within first lumen 48. Stents 50 are preferably composed of a resilient material such as stainless steel or Nitinol so as to self-expand from the collapsed configuration to a radially expanded configuration when deployed from first lumen 48. While stents 50 as illustrated have a wave-like or undulating pattern in a plurality of interconnected circumferential members, the pattern illustrated is merely exemplary and the stents of the invention may have any of a variety of strut shapes, patterns, and geometries. From 2 up to 10 or more stents may be carried by outer shaft 24. Optionally, a valve member 49 is mounted within first lumen 48 to facilitate separating those stents 50 to be deployed from those to remain within outer shaft 24, as described in co-pending U.S. patent application Ser. No. 10/412,714, filed Apr. 10, 2003, which is incorporated herein by reference.

Coupled with inner shaft 28 is an expandable stent bumper 60. In various embodiments, stent bumper 60 may comprise an expandable wire or mesh basket, an expandable ring, shape-memory members such as petals, blades, prongs or other protrusions, or any of a number of other configurations. In a preferred embodiment, as shown, stent bumper 60 is an inflatable balloon. In some embodiments, stent bumper 60 is inflatable via an inflation lumen disposed within inner shaft 28. Such an inflation lumen may alternatively be disposed on an outer surface of inner lumen 28 or the like. In some embodiments, stent bumper 60 may be attached to, or a proximal extension of, a nosecone 36 of delivery catheter 20. When expanded, stent bumper 60 helps control the deployment of stents 50. For example, if stent bumper 60 is expanded and a stent 50' is deployed out of the distal end of catheter body 46, stent bumper 60 has a diameter large enough, in its expanded configuration, to stop deployed stent 50' from moving distally, thus preventing "watermelon seeding" of stent 50'. The operation of stent bumper 60 will be described further below with reference to subsequent drawing figures.

Handle assembly 21 has a rotatable retraction knob 52 coupled to a shaft housing 53, to which outer shaft 24 is fixed. By rotating retraction knob 52, outer shaft 24 may be retracted proximally relative to pusher 26 and inner shaft 28. A switch 56 engages and disengages pusher 26 with outer shaft 28, so that pusher 26 either moves with outer shaft 24 or remains stationary as outer shaft 24 is retracted. Indicia 58 on shaft housing 53 indicate the extent of retraction of outer shaft 28 by distance, number of stents, or other suitable measure. Other aspects of handle assembly 21 are described in co-pending application Ser. No. 10/746,466, filed Dec. 23, 2003, which is hereby incorporated by reference. Except as stated otherwise, any of the embodiments of the stent delivery catheter described below may incorporate the features, and be otherwise constructed as, just described.

With reference now to FIGS. 2A and 2B, in some embodiments, a stent delivery catheter 180 includes an stent bumper 160 comprising an inflatable balloon. Delivery catheter 180 has a plurality of stents 182 disposed in an outer shaft 184. An inner shaft 186, with a distal nosecone 190, extends through outer shaft 184 and stents 182 and is axially movable relative thereto. A pusher shaft (not shown) is slidably disposed over inner shaft 186 and engages stents 182 for purposes of deploying stents 182 from outer shaft 186 and repositioning the remaining stents 182 within outer shaft 186, as in earlier embodiments. In this embodiment, stents 182 comprise a plurality of struts 191 forming a series of rings 192 interconnected at joints 193. Each ring 192 has a series of closed cells 194 interconnected circumferentially and having an "I" shape in the unexpanded configuration. Other aspects of stents 182 are described in co-pending U.S. application Ser. No. 10/738,666, which was previously incorporated by reference.

As outer shaft 184 is retracted to deploy one or more stents 182, at least a distal ring 192' is configured to expand into engagement with stent bumper 160 before the entire length of stent 182 is deployed from outer shaft 184 (FIG. 2A). Once distal ring 192' is engaged with stent bumper 160, the remainder of stent 182 is deployed (FIG. 2B), stent bumper 160 thus preventing "watermelon seeding" of stent 182 from catheter 180. Each stent 182 has at least two, and preferably four or more rings 192, each ring being about 2-5 mm in length, giving stent 182 an overall length of at least about 8-20 mm. Of course, stents of shorter or longer length are also contemplated within the scope of the invention. Lesions longer than each stent 182 may be treated by deploying multiple stents 182 end-to-end. Advantageously, each stent 182 can be deployed precisely at a desired spacing from a previously-deployed stent 182 because stent bumper 160 prevents unwanted overlapping of, or gaps between, stents 182 caused by watermelon seeding.

Rings 192 are preferably formed from a common piece of material and are integrally interconnected at joints 193, making joints 193 relatively rigid. In this embodiment, the majority of flexibility between rings 192 is provided by struts 191 rather than by joints 193. Alternatively, joints 193 may comprise welded connections between rings 192 which are also fairly rigid. As a further alternative, joints 193 may comprise hinge or spring structures to allow greater deflection between adjacent rings 192.

In various alternative embodiments, any of a number of alternative stents with alternative designs, shapes, sizes, materials and/or the like may be used. For example, a number of exemplary self-expanding stents that may be used with delivery catheter 180 are described in co-pending U.S. patent application Ser. Nos. 10/879,949 and 10/738,666, which were previously incorporated by reference. Stents 192 may be made of any suitable material, such as but not limited to Nitinol™, a superelastic alloy, stainless steel, cobalt chromium, other resilient metals, resilient polymers or the like. In some embodiments, stent 192 may be balloon expandable, rather than self-expanding, although this description focuses on the preferred self-expanding embodiments.

Various alternative types of interconnecting structures between adjacent stents and between the stents and the pusher shaft are also possible within the scope of the invention, including those described in co-pending application Ser. No. 10/738,666, previously incorporated by reference. Such interconnecting structures may also be breakable or frangible to facilitate separation as the stent expands. In addition, a mechanism such as an expandable balloon or cutting device may be disposed at the distal end of delivery catheter 180 to assist in separating stents 192 upon deployment. Further, the interconnections between stents may be different than the interconnection between the proximal-most stent and the pusher shaft. For example, the pusher shaft may have hooks, magnets, or other mechanisms suitable for releasably holding and maintaining traction on the proximal end of a stent until it is deployed.

Figure 3D:
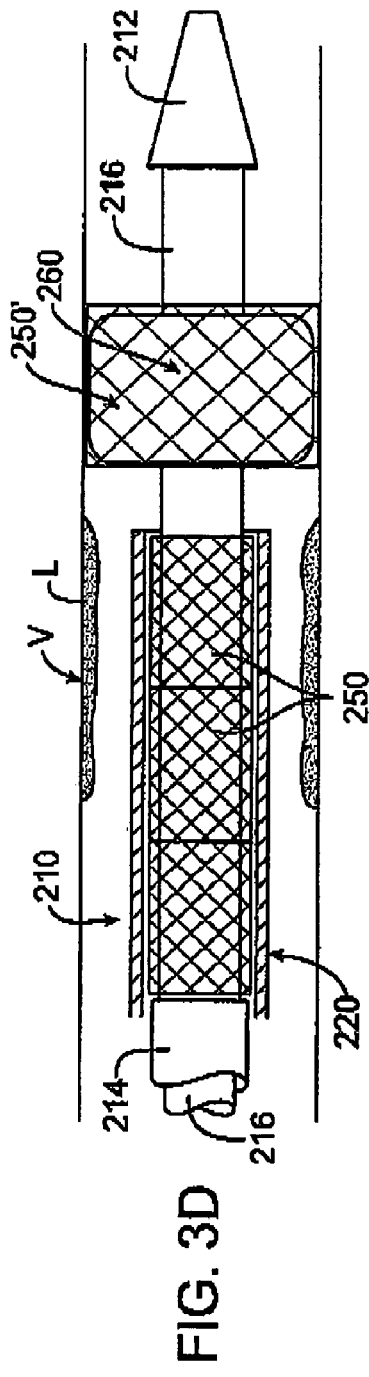

Referring to FIGS. 3A-3F, a method for deploying stents in a vessel is shown schematically. In FIG. 3A, a stent delivery catheter 210 is positioned within a vessel V, such that a nosecone 212 attached to the distal end of an inner shaft 216 of catheter 210 is distal to a lesion L. A stent bumper 260 coupled with inner shaft 216 is expanded (in this case an inflated balloon) to contact the vessel wall. Multiple stents 250 (or stent segments) are housed within an outer shaft 220 or sheath of catheter 210, and a pusher 214 is used to maintain the axial position of stents 250 relative to outer shaft 220.

In FIG. 3B, outer shaft 220 is retracted relative to stents 250 and inner shaft 216, while pusher 214 maintains the relative axial position of stents 250. As outer shaft 220 is retracted, a distal stent 250' begins to be deployed out of its distal end. Distal stent 250' contacts stent bumper 260, which prevents stent 250' from ejecting ("watermelon seeding") distally. FIG. 3C shows distal stent 250' fully deployed within the vessel V.

Figure 3E:
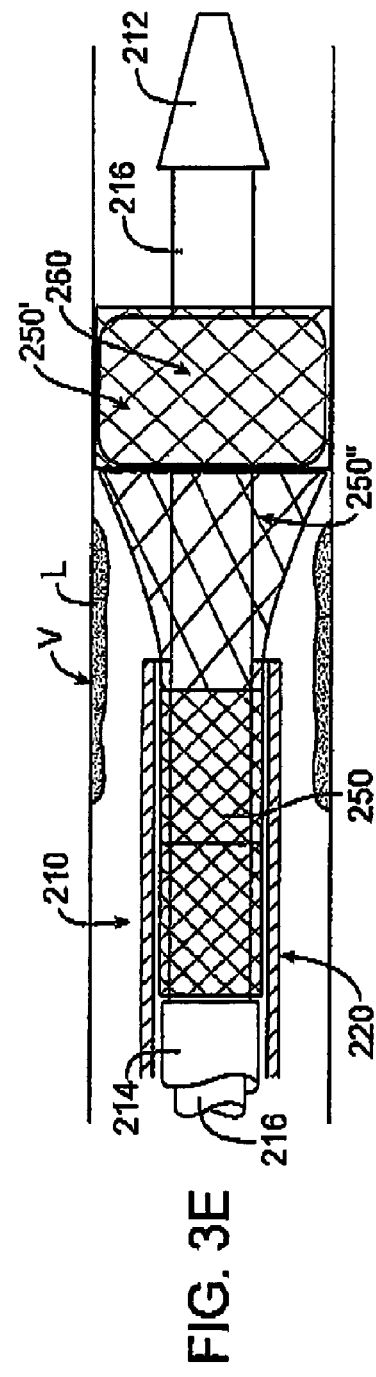
Figure 3F:
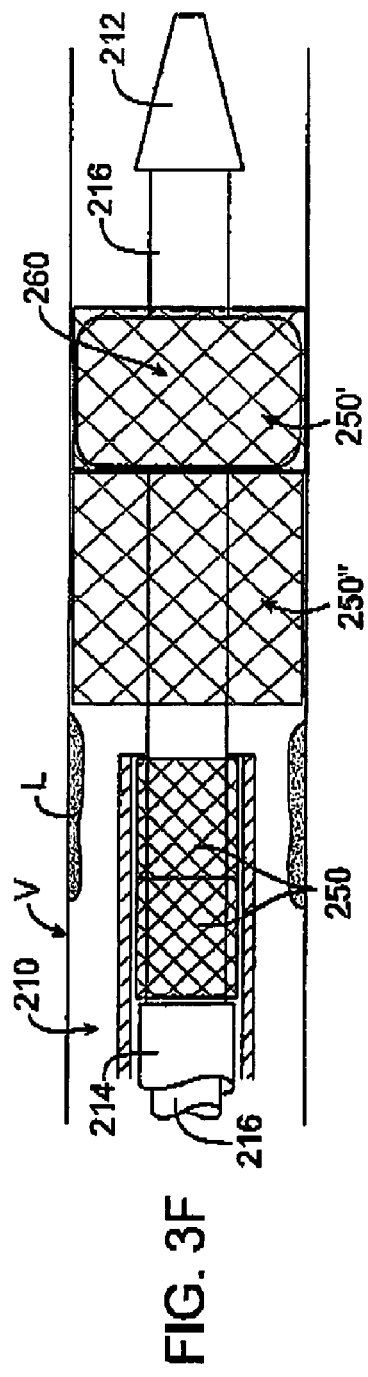

As shown in FIG. 3D, after a first distal stent 250' has been fully deployed, stent bumper 260 may be deflated, repositioned with distal stent 250', and re-expanded. In some cases, this re-expansion helps further expand distal stent 250', thus enhancing its ability to prop open the vessel V. Turning to FIG. 3E, after re-expansion of stent bumper 260, outer shaft 220 may again be retracted relative to stents 250 and inner shaft 216, thus deploying a second distal stent 250". Second distal stent 250" contacts stent bumper 260, thus again avoiding watermelon seeding, which might cause sterns 250" and 250' to overlap. FIG. 3F shows first distal stent 250' and second distal stein 250" fully deployed within the vessel. This process may be repeated as many times as desired, to deploy as many stents 250 (or stent segments) as desired.

Referring now to FIGS. 4A-4C, in an alternative embodiment, a stent delivery catheter 310 may include a stent bumper 360 that comprises an elongate inflatable balloon. In such an embodiment, first distal stent 250' is deployed the same way as shown in FIGS. 3A-3C. As shown in FIG. 4A, after deployment of first distal stent 250', a sheath 322 disposed over a proximal portion of stent bumper 360 is retracted proximally to expose an additional portion of stent bumper 360, and the newly exposed portion of the inflatable balloon stent bumper 360 is inflated within first distal stent 250'. As described above, stent bumper 360 in some embodiments may be used to further expand an already-expanded distal stent 250'.

As shown in FIG. 4B, second distal stent 250" is then deployed from the distal end of outer shaft 220 to contact stent bumper 360. In FIG. 4C, second distal stent 250" is fully deployed, sheath 322 has been retracted farther proximally, and an additional portion of stent bumper 360 has been inflated within second distal stent 250". This process may be repeated as many times as desired to deploy as many stents 250 as desired.

Referring now to FIG. 5, an alternative embodiment of a stent delivery catheter 410 includes an expandable wire structure 460 that acts as a stent bumper. Wire structure 460 acts analogously to the stent bumpers described above. In the embodiment shown, wire structure 460 is made of shape memory, super-elastic or other resilient material and assumes its expanded shape when exposed from the distal end of a sheath 422. Sheath 422 may be retracted farther proximally to expose additional portions of wire structure 460 to help deploy additional stents 250. In other embodiments, a wire ring or tube, expandable wire basket, mesh basket or the like may be pushed by a proximal pusher member or pulled by a puller coupled to its distal end to force the expandable stent bumper to buckle or otherwise expand.

In another embodiment, and with reference now to FIG. 6, a stent delivery catheter 510 include a stent bumper 560 comprising multiple self-expanding petals 562 (or alternatively prongs, blades, bristles or the like) coupled to an outer shaft 522 slidable over inner shaft 216. Petals 562 are normally disposed within nosecone 212 and deploy/expand when inner shaft 216, to which nosecone 212 is attached, is advanced distally relative to outer shaft 522, thereby exposing petals 562. Nosecone 212 may be advanced further to allow greater expansion of petals 562 or to expose additional sets of petals 562. Petals 562 may be made of metal, polymer or any other suitable resilient material(s).

Figure 7:
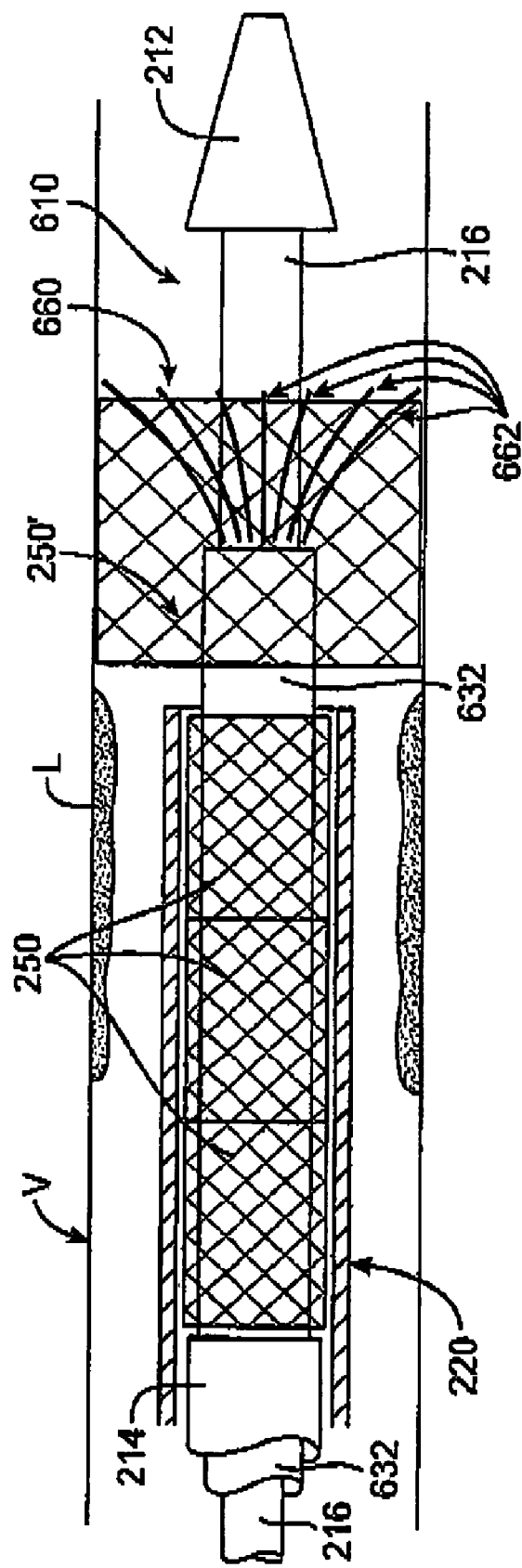
FIG. 7 is a side cross-sectional view of a distal portion of a prosthesis delivery catheter with a stent bumper in a vessel according to another embodiment of the present invention.

Referring now to FIG. 7, in another embodiment, a stent delivery catheter 610 includes a stent bumper 660 comprising multiple self-expanding prongs 662 coupled with inner shaft 216. Before deployment, prongs 662 are disposed with a sheath 632 slidably disposed over inner shaft 216. When sheath 632 is retracted proximally relative to inner shaft 216 and/or inner shaft 216 is advanced relative to sheath 632, prongs 662 are exposed, thus allowing them to assume their expanded configuration, as shown. After deploying first stent 250', which is prevented from watermelon seeding by stent bumper 660, sheath 632 may be retracted farther proximally and/or inner shaft 216 may be advanced farther distally to expose a second set of prongs 662 (not shown). A second stent 250 may then be deployed to contact the second set of prongs 662. In various embodiments, any number of stent bumpers 660/sets of prongs 662 may be included, for promoting deployment of any number of stents 250. Prongs 662 may be made of any resilient material, such as Nitinol, spring stainless steel, or other shape-memory or super-elastic materials.

While the above is a complete description of the preferred embodiments of the invention, various alternatives, modifications, improvements and additions are possible without departing from the scope thereof, which is defined by the claims.

What is claimed is:

1. A catheter system for delivery of a stent to a body lumen comprising:
   a stent delivery catheter comprising:
      a sheath having a first lumen;
      a shaft extending through the first lumen and slidable relative to the sheath;
      a stent bumper mounted to the shaft distally of the sheath and movable from a contracted shape to an expanded shape,
   wherein the stent comprises an inflatable balloon, and
   wherein the balloon comprises an elongate balloon having an axial length at least as long as two stent segments;
   a plurality of self-expanding stent segments carried within the first lumen in a collapsed configuration, the stent segments being adapted to resiliently expand from the collapsed configuration to an expanded configuration,
   wherein the stent segments are deployable from the first lumen so as to resiliently expand into the expanded, configuration, the stent bumper being expandable independently of the stent segments and configured in the expanded shape to engage a first stent segment during deployment thereof to maintain its position relative to an adjacent stent segment disposed proximal to the first stent segment; and
   an inner sheath disposed over the balloon, wherein the inner sheath is retractable to expose a portion of the balloon to allow it to be inflated from the contracted shape to the expanded shape.

2. A system as in claim 1, wherein the balloon is adapted to be expanded within one or more deployed stent segments to further expand the segments.

3. A method of delivering a stent to a body lumen comprising:
   positioning a stent delivery catheter in the body lumen, the delivery catheter carrying at least first and second stent segments;
   expanding a stent bumper on the deliver catheter,
   wherein expanding the stent bumper comprises inflating a balloon;
   releasing the first stent segment from the delivery catheter into the body lumen after the stent bumper has been fully expanded, the first stent segment resiliently self-expanding into an expanded configuration in the body lumen, wherein the stent bumper expands independently of the first stent segment and engages the first stent segment during expansion thereof to maintain its position relative to the delivery catheter;
   before releasing the second stent segment,
   deflating the balloon;
   positioning the deflated balloon within the expanded first stent segment;
   inflating the balloon, wherein the balloon engages the second stent segment during expansion thereof to maintain its position relative to the delivery catheter and the first segment; and
   releasing the second stent segment from the delivery catheter into the body lumen adjacent to the first stent segment.

4. A method as in claim 3, wherein inflating the balloon within the first segment further expands the first segment.

5. A method as in claim 3, further comprising:
   deflating the balloon;
   positioning the deflated balloon within the expanded second stent segment; and
   inflating the balloon, wherein the balloon engages a third stent segment during expansion thereof to maintain its position relative to the delivery catheter and the first and second segments.

6. A method of delivering a stent to a body lumen comprising:
   positioning a stent delivery catheter in the body lumen, the delivery catheter carrying at least first and second stent segments;
   expanding a stent bumper on the delivery catheter;
   wherein expanding the stent bumper comprises inflating a balloon;
   releasing the first stent segment from the delivery catheter into the body lumen after the stent bumper has been fully expanded, the first stent segment resiliently self-expanding into an expanded configuration in the body lumen, wherein the stent bumper expands independently of the first stent segment and engages the first stent segment during expansion thereof to maintain its position relative to the delivery catheter;
   before releasing a second stent segment,
   exposing an additional portion of the balloon from the distal end of an inner sheath, the additional portion disposed within the expanded first stent segment;
   inflating the balloon, wherein the balloon engages the second stent segment during expansion thereof to maintain its position relative to the delivery catheter and the first segment; and releasing the second stent segment from the delivery catheter into the body lumen adjacent to the stent segment.

7. A method as in claim 6, wherein inflating the additional portion of the balloon further expands the expanded first stent segment.

8. A catheter system for delivery of a stent to a body lumen comprising:
- a stent delivery catheter comprising:
  - a sheath having a first lumen;
  - a shaft extending through the first lumen and slidable relative to the sheath;
  - a stent bumper mounted to the shaft distally of the sheath and movable from a contracted shape to an expanded shape,
  - wherein the stent bumper comprises a shape memory element adapted to resiliently expand to the expanded shape when unconstrained;
- a plurality a self-expanding stent segments carried within the first lumen in a collapsed configuration, the stent segments being adapted to resiliently expand from the collapsed configuration to an expanded configuration,
- wherein the stent segments are deployable from the first lumen so as to resiliently expand into the expanded configuration, the stent bumper being expandable independently of the stent segments and configured in the expanded shape to engage a first stent segment during deployment thereof to maintain its position relative to an adjacent stent segment disposed proximal to the first segment; and
- a constraining member on the delivery catheter axially movable relative to the stent bumper and adapted to constrain the shape memory element in the contracted shape.

9. A catheter system for delivery of a stent to a body lumen comprising:
- a stent delivery catheter comprising:
  - a sheath having a first lumen;
  - a shaft extending through the first lumen and slidable relative to the sheath;
  - a stent bumper mounted to the shaft distally of the sheath and movable from a contracted shape to an expanded shape,
  - wherein the stent bumper comprises an inflatable balloon,
  - wherein the balloon comprises an elongate balloon having an axial length at least as long as two stent segments;
- a plurality of self-expanding stent segments carried within the first lumen in a collapsed configuration, the stent segments having a plurality of struts defining a plurality of apertures and being adapted to resiliently expand from the collapsed configuration to an expanded configuration,
- wherein the stent segments are deployable from the first lumen so as to resiliently expand into the expanded configuration, the stent bumper being expandable independently of the stent segments and configured in the expanded shape to engage a first stent segment without passing through the apertures to maintain the position of the first stent segment relative to the stent delivery catheter; and
- an inner sheath disposed over the balloon, wherein the inner sheath is retractable to expose a portion of the balloon to allow it to be inflated from the contracted shape to the expanded shape.

10. A system as in claim 9, wherein the balloon is adapted to be expanded within one or more deployed stent segments to further expand the segments.

11. A system as in claim 10, wherein the balloon in the expanded shape is adapted to further expand the deployed first stent segment.

12. A catheter system for delivery of a stent to a body lumen comprising:
- a stent delivery catheter comprising:
  - a sheath having a first lumen;
  - a shaft extending through the first lumen and slidable relative to the sheath;
  - a stent bumper mounted to the shaft distally of the sheath and movable from a contracted shape to an expanded shape,
  - wherein the stent bumper comprises a shape memory element adapted to resiliently expand to the expanded shape when unconstrained;
- a plurality of self-expanding stent segments carried within the first lumen in a collapsed configuration, the stent segments having a plurality of struts defining a plurality of apertures and being adapted to resiliently expand from the collapsed configuration to an expanded configuration,
- wherein the stent segments are deployable from the first lumen so as to resiliently expand into the expanded configuration, the stent bumper being expandable independently of the stent segments and configured in the expanded shape to engage a first stent segment without passing through the apertures to maintain the position of the first stent segment relative to the stent delivery catheter; and
- a constraining member on the delivery catheter axially movable relative to the stent bumper and adapted to constrain the shape memory element in the contracted shape.

* * * * *

UNITED STATES PATENT AND TRADEMARK OFFICE
CERTIFICATE OF CORRECTION

PATENT NO. : 7,300,456 B2
APPLICATION NO. : 10/944282
DATED : November 27, 2007
INVENTOR(S) : Bernard Andreas et al.

It is certified that error appears in the above-identified patent and that said Letters Patent is hereby corrected as shown below:

In claim 1, column 9, line 51, delete "wherein the stent comprises" and insert --wherein the stent bumper comprises--.

In claim 3, column 10, line 11, delete "deliver" and insert --delivery--.

In claim 6, column 11, line 2, delete "to the stent" and insert --to the first stent--.

In claim 8, column 11, line 19, delete "a plurality a" and insert --a plurality of--.

In claim 8, column 11, line 29, delete "to the first" and insert --to the first stent--.

Signed and Sealed this

Tenth Day of June, 2008

JON W. DUDAS
*Director of the United States Patent and Trademark Office*